US007742932B2

(12) United States Patent
Segal

(10) Patent No.: US 7,742,932 B2
(45) Date of Patent: Jun. 22, 2010

(54) HYPER-FRACTIONATION OF TRANSMISSION HISTORY FOR MEDICAL DIAGNOSTIC SOFTWARE

(75) Inventor: Michael M. Segal, Chestnut Hill, MA (US)

(73) Assignee: SimulConsult, Inc., Chestnut Hill, MA (US)

( * ) Notice: Subject to any disclaimer, the term of this patent is extended or adjusted under 35 U.S.C. 154(b) by 1901 days.

(21) Appl. No.: 10/350,217

(22) Filed: Jan. 22, 2003

(65) Prior Publication Data
US 2004/0143455 A1    Jul. 22, 2004

(51) Int. Cl.
G06Q 10/00      (2006.01)
G06Q 50/00      (2006.01)
G06Q 40/00      (2006.01)
A61B 5/00       (2006.01)
G06F 19/00      (2006.01)

(52) U.S. Cl. .................................. 705/3; 705/2; 705/4
(58) Field of Classification Search .............. 705/2, 705/3, 4
See application file for complete search history.

(56) References Cited

U.S. PATENT DOCUMENTS

| | | | | |
|---|---|---|---|---|
| 5,752,976 | A * | 5/1998 | Duffin et al. | 607/32 |
| 5,902,234 | A * | 5/1999 | Webb | 600/300 |
| 6,033,365 | A * | 3/2000 | von Zitzewitz | 600/300 |
| 6,539,101 | B1 * | 3/2003 | Black | 382/124 |
| 6,579,231 | B1 * | 6/2003 | Phipps | 600/300 |
| 2001/0056358 | A1 * | 12/2001 | Dulong et al. | 705/2 |
| 2002/0019584 | A1 * | 2/2002 | Schulze et al. | 600/300 |
| 2002/0087359 | A1 * | 7/2002 | Bocionek | 705/2 |
| 2002/0128860 | A1 * | 9/2002 | Leveque et al. | 705/2 |
| 2003/0125609 | A1 * | 7/2003 | Becker | 600/300 |
| 2003/0191665 | A1 * | 10/2003 | Fitzgerald et al. | 705/2 |

OTHER PUBLICATIONS

Avitzur, "How Neurologists Use the Internet to Enhance Clinical Decision-Making," *Neurology Today* 2:32-34, 2002 (http://journals.lww.com/neurotodayonline/Fulltext/2002/11000/How_Neurologists_Use_the_Internet_To_Enhance.13.aspx, Retrieved on Jan. 14, 2010).

Bankier et al., "POSSUM: The Microcomputer Laser-Videodisk Syndrome Information System," *Ophthalmic Paediatr. Genet.* 10:51-52, 1989.

Barnett et al., "DXplain: An Evolving Diagnostic Decision-Support System," *J. Am. Med. Assoc.* 258:67-74, 1987.

Hamosh et al., "Online Mendelian Inheritance in Man (OMIM), a Knowledgebase of Human Genes and Genetic Disorders," *Nucleic Acids Res.* 30:52-55, 2002.

Ramnarayan et al., "ISABEL: a Web-Based Differential Diagnostic Aid for Paediatrics: Results from an Initial Performance Evaluation," *Arch. Dis. Child* 88:408-413, 2003.

(Continued)

*Primary Examiner*—Gerald J. O'Connor
*Assistant Examiner*—Amber Altschul
(74) *Attorney, Agent, or Firm*—Clark & Elbing LLP; Kristina Bieker-Brady; Michael A. Robinson

(57) ABSTRACT

The difficulties in incorporating transmission history into medical diagnostic software are non-obvious. These are addressed here with systems and methods for hyper-fractionation of transmission history in a way that allows the full power of this information to be used in medical diagnostic software.

37 Claims, 6 Drawing Sheets

OTHER PUBLICATIONS

Tamarin, "Principles of Genetics," Fourth Edition, Chapter 5: Pedigree Analysis, 82-85, 1993.

DXplain, http://dxplain.org/dxp/dxp.pl (Retrieved on Jan. 14, 2010).

Isabel Healthcare, http://www.isabelhealthcare.com/home/default (Retrieved on Jan. 14, 2010).

OMIM Home, http://www.ncbi.nlm.nih.gov/sites/entrez?db=omim (Retrieved on Jan. 14, 2010).

POSSUM Web, http://www.possum.net.au (Retrieved on Jan. 14, 2010).

SimulConsult, http://www.simulconsult.com/ (Retrieved on Jan. 14, 2010).

"Fractionate," Merriam-Webster Online Dictionary, http://www.merriam-webster.com/dictionary/fractionation (Retrieved on Jan. 20, 2010).

"Fractionation," Thefreedictionary.com, http://medical-dictionary.thefreedictionary.com/p/fractionation (Retrieved on Jan. 20, 2010).

* cited by examiner

Specify transmission history:

Fill in as much as possible; denominators influence weight of a negative history:

| | | | | |
|---|---|---|---|---|
| Mother affected | ○ Yes | ○ No | ● Unknown | |
| Father affected | ● Yes | ○ No | ○ Unknown | |
| Older sisters affected | | 0 ▼ of | 1 ▼ | older |
| Older brothers affected | | 0 ▼ of | 0 ▼ | older |
| Maternal uncles affected | | 0 ▼ of | 0 | total |
| | | | 1 | |
| Other nearby individuals affected | | 0 ▼ of | 2 | total |
| | | | 3 | |
| Parental consanguinity | | 1st cousin | 4 | ▼ |
| | | | 5 | |
| | | | 6 | |

Help    Finish

Figure 3:

| Differential including: Tics (limbs or face), grimacing or abnormal v | | ☑ Incidence |
|---|---|---|
| Diseases in Differential | Relative Probability | ☑ Onset ages |
| Huntington chorea, juvenile akinetic-rigid form | ▓▓▓▓▓▓▓▓▓ | |
| Neurodeg. with brain iron accum. (Hallervorden-Sp: | ▓▓▓ | |
| Niemann-Pick disease, juvenile (C) | | |
| Gaucher disease III (subacute juvenile neuronopathi | | |
| Adrenoleukodystrophy (ALD), X-linked | | |
| Chorea acanthocytosis (neuroacanthocytosis) | | |
| Wilson disease (hepatolenticular degeneration) | | Profile finding |
| GM2 gangliosidosis, juvenile (type III) | | Resources |
| Alexander disease, juvenile | | Useful |
| Dystonia musculorum deformans I (torsion dystonia | | findings |
| Ceroid lipofuscinosis, juvenile (Spielmeyer-Vogt, Ba | | Reference |
| Rett syndrome | | Modify |
| Friedreich ataxia | | Edit patient |
| Amyotrophic Lateral Sclerosis (ALS): juvenile reces | | Search |
| Hereditary spastic paraplegia, recessive | | Start   Help |
| Spinocerebellar ataxia (SCA) 2, Cuban type | | |

Figure 4:

| Differential including ⚙ | Family history of a similar disorder | ☑ Incidence |
|---|---|---|
| Diseases in Differential | Relative Probability | ☑ Onset ages |
| Huntington chorea, juvenile akinetic-rigid form | ▓▓▓▓▓▓▓ | |
| Neurodeg. with brain iron accum. (Hallervorden-Sp: | | |
| Niemann-Pick disease, juvenile (C) | | |
| Chorea acanthocytosis (neuroacanthocytosis) | | |
| Gaucher disease III (subacute juvenile neuronopathi | | |
| Adrenoleukodystrophy (ALD), X-linked | | |
| Wilson disease (hepatolenticular degeneration) | | Profile finding |
| Dystonia musculorum deformans I (torsion dystonia) | | Resources |
| GM2 gangliosidosis, juvenile (type III) | | Useful |
| Alexander disease, juvenile | | findings |
| Ceroid lipofuscinosis, juvenile (Spielmeyer-Vogt, Ba | | Reference |
| Spinocerebellar ataxia (SCA) 2, Cuban type | | Modify |
| Spinocerebellar ataxia (SCA) 10 | | Edit patient |
| Spinocerebellar ataxia (SCA) 3 type I, Machado-Jos | | Search |
| Rett syndrome | | Start  Help |
| Friedreich ataxia | | |

Figure 6:

| Neurological Syndromes - SimulConsult | | |
|---|---|---|
| Justifying Dx of Neurodeg. with brain iron accum. (Hallervorden-Spatz, I | | |
| Findings PRESENT in this Patient | Now | Later |
| 10 Dysphagia (swallowing difficulty) | | |
| 10 Dystonic posturing (torsion dystonia, torticolis incl | | |
| 6y Gait poor, clumsy, shuffling or unsteady | | |
| 6y Speech: abnormal sound character (dysarthria, slu | | |
| 10 Tics (limbs or face), grimacing or abnormal vocali | | |
| 10 Seizures, nonfebrile | | |
| Findings ABSENT in this Patient | By Now | Later |
| x Family history of a similar disorder | | |

TOP
In order of Differential

Incidence: Low
Rx: None yet

☑ Onset ages

Differential diagnosis

Profile finding
Resources
Useful findings
Citation
Modify
Edit patient
Search / find
Start  Help

HYPER-FRACTIONATION OF TRANSMISSION HISTORY FOR MEDICAL DIAGNOSTIC SOFTWARE

BACKGROUND OF THE INVENTION

The heritability of many diseases is well defined. Accordingly, information about relatives and their health or disease has become an essential part of history-taking in the process of medical diagnosis. However, it has been difficult to use such information about family history (or more generally all forms of history about "transmission" of diseases) in computerized medical diagnostic tools. In part, this is because of the complexity of medical genetics in which many different forms of inheritance are possible however, another significant barrier are other difficulties in representing such transmission history. There are 6 main types of inheritance patterns for diseases that have been well described in the medical literature:

1. Autosomal dominant: a gene on a non-sex chromosome causes disease when one copy is defective. If one parent has such a gene, each child typically has a 0.5 chance of getting the disease.
2. Autosomal recessive: a gene on a non-sex chromosome causes disease when both copies are defective. If both parents have such a gene, each child typically has a 0.25 chance of getting the disease.
3. X-linked dominant: a gene on an X chromosome causes disease when one copy is defective. Males typically have one X chromosome, females typically have two. Females typically get an X chromosome from each parent, males typically get one only from the mother.
4. X-linked recessive: a gene on an X chromosome causes disease when all copies are defective (typically one for males and two for females). Females typically get an X chromosome from each parent, males typically get one only from the mother.
5. Mitochondrial (dominant): a mitochondrial gene causes disease when a high percentage of copies are defective. Mitochondrial genes come essentially only from the mother.
6. Y-linked (dominant): a gene on the Y chromosome causes disease when defective. Only males have Y chromosomes and they are inherited from the father.

These forms of transmission are further complicated by:
Spontaneous mutation—appearance of a genetic defect despite the presence of a normal gene genes in parents.
Penetrance—not all people with a pathogenic number of defective genes exhibit the disease. The fraction who exhibit the disease is called penetrance.
Consanguinity—close genetic relationship of parents, for example first cousins, increasing the chance of recessive diseases.
Non-paternity or other false reports of family history.

In addition, transmission can be environmental or contagious.

SUMMARY

These difficulties in incorporating transmission history into medical diagnostic software are non-obvious. These are addressed here with systems and methods for hyper-fractionation of transmission history in a way that allows the full power of this information to be used in medical diagnostic software.

BRIEF DESCRIPTION OF THE DRAWINGS

The present disclosure may be better understood and its numerous features and advantages made apparent to those skilled in the art by referencing the accompanying drawings.

FIG. 1 is representative screen shot of the modify disease screen, according to one embodiment of the invention.

FIG. 2 is a representative screen shot of the transmission details screen, according to one embodiment of the invention.

FIG. 3 is a representative screen shot of the diagnostic probabilities output, according to one embodiment of the invention.

FIG. 4 is a representative screen shot depicting the presence of a family history, according to one embodiment of the invention.

FIG. 5 and 6 are representative screen shots of one embodiment of the invention displaying Dr. Malanga's case.

DETAILED DESCRIPTION

Figure 5:
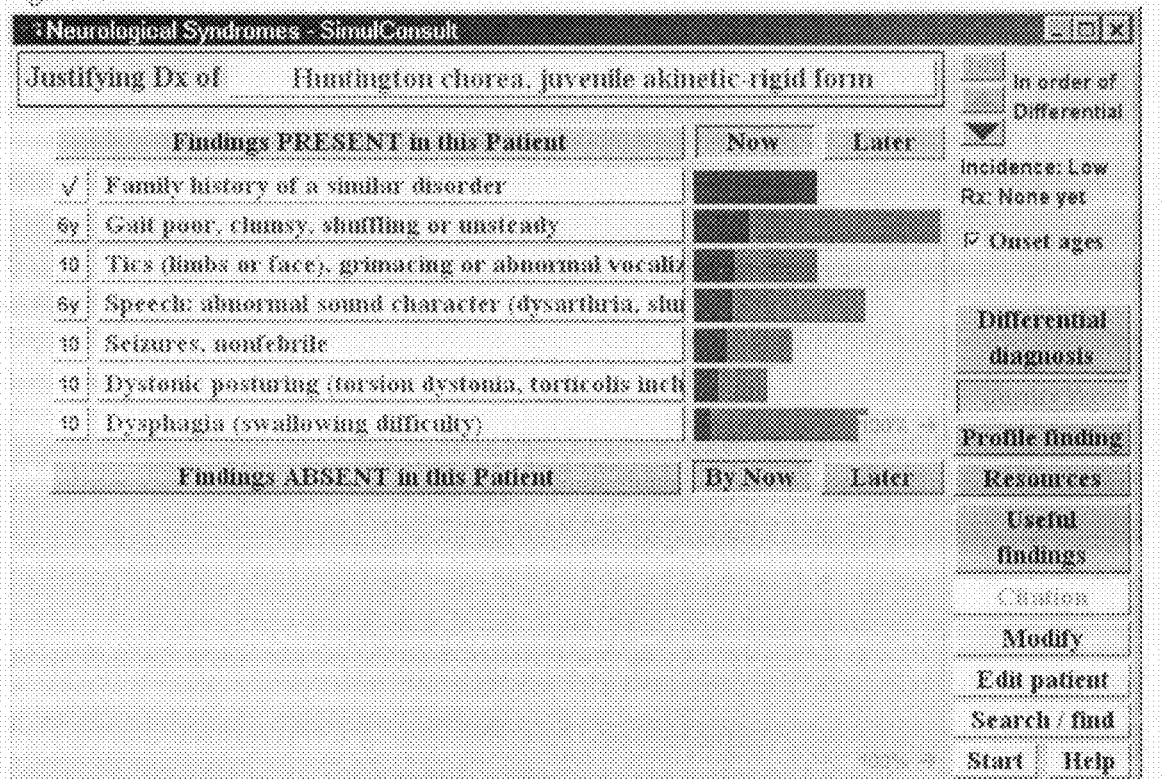

Applying Transmission Information in Medical Diagnostic Software

A simplistic approach to applying family history to medical diagnostic software would be to consider family history as another "finding" in the medical history, similar to "seizures". One could record the inheritance pattern for each disease and assign a probability of finding a family history to each disease based on the type of transmission. For example, one could estimate from population data that a positive family history is present in 15% of patients with autosomal recessive diseases and 75% of people with autosomal dominant diseases. Finding a positive family history would then elevate the probability of autosomal dominant diseases over autosomal recessive diseases by five-fold using standard Bayesian reasoning models popularized during the 1960s.

However, this approach fails to capture much important information:
Nature of family history: having a parent with a disease is most suggestive of dominant inheritance, while having only siblings with a disease is most suggestive of recessive inheritance.
Missing information in the history: if someone has no siblings one would not expect a family history of a recessive disease because the parents are likely to be carriers with only one defective gene ("heterozygotes"), and thus unaffected by the illness.
Deviations from ideal inheritance models: the degree of spontaneous mutations and gene penetrance can modify the expected family history dramatically.

A more sophisticated approach and method would be to compute an expected family history for each disease based on all these factors. Yet even this approach is inadequate because many diseases will have a similar expected family history under many circumstances. For example, in a case in which all relatives in a large family are examined and mutations and non-penetrance are not factors, the expected family history for all types of inherited disease would have probability 1.0 and the discriminating value of a positive finding of family history in a patient would be zero, just as the discriminating value of finding "seizures" in a patient would be zero if all diseases exhibited seizures.

Clearly, more sophisticated approaches are needed. This application describes systems and methods of hyper-fractionating information about disease transmission information for use in software that combines detailed transmission history information from a particular patient to discriminate properly among various diseases, based on the match between the patient's family history and the known information about the disease. This hyper-fractionation of transmission history information has been implemented as part of a medical diagnostic software program "SimulConsult Neurological Syndromes." Thus, the invention described herein may be realized as a computer program running on a data processing platform, that may optionally allow for access and operation over a data network, such as the Internet. With these systems and methods, transmission information about patients is handled in a way that uses detailed information about disease transmission to properly discriminate between different forms of transmission such as different forms of inheritance.

Transmission Information Stored in the Database About Each Disease

Transmission type: input using a pull-down choice component, including the 6 genetic forms above as well as contagious and environmental.

Penetrance: as a percentage with a default of 100

Spontaneous mutations: as a percentage with a default of 0.

Figure 1:
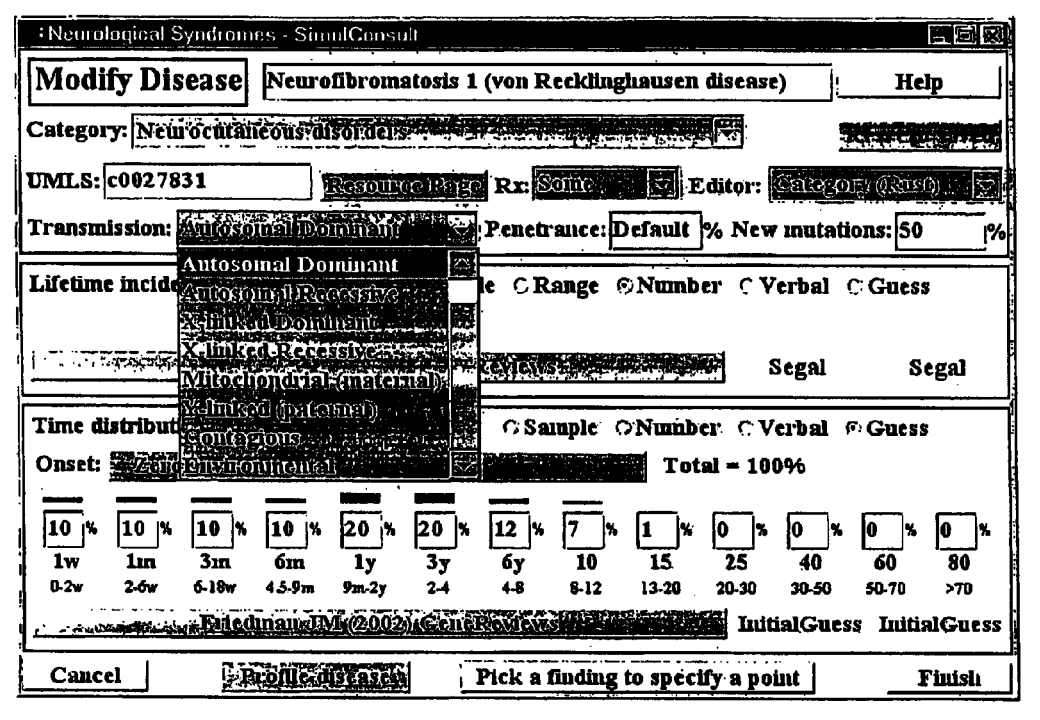

This is illustrated on the Modify Disease screen of the software, shown in FIG. 1.

Information About Transmission History That can be Entered Into the Software for Each Patient The user indicates information about the following:
Mother
Father
Sisters, typically older due to onset ages
Brothers, typically older due to onset ages
Maternal uncles
Other nearby individuals
Parental consanguinity (first cousin and so forth)

This is illustrated on the Transmission Details screen of the software, shown in FIG. 2. The information set out above is merely illustrative of the type of information that may be collected about transmission history and other information may also be collected in combination, or instead of the above identified information. Moreover, other techniques besides questionnaires may be employed for capturing and gathering transmission history information, and the such variations are deemed to fall within the scope of the invention.

Systems and Methods for Fractionating Transmission History in Diagnosing Diseases To understand the need for new systems and methods of dealing with family history, consider in more detail the above mentioned example in which family history is collected from many relatives, resulting in an expected family history probability approaching 1.0 for diseases with all types of inheritance. Consider the specific case in which it is determined that some siblings of the patient are affected by the disease, but not parents. In this case, there is a positive family history for autosomal recessive transmission, but a negative family history for autosomal dominant transmission. The simplistic model would have blurred such information by doing the following analysis:

Patient: positive generic "family history"
Diseases: high probability for finding family history assigned to diseases with all types of inheritance
Result: little discriminative ability since probability of all diseases elevated by generic positive family history Such a simplistic result is wrong, ignoring the discriminative information present in the history. A realization of the systems and methods described herein is that to use transmission history in computerized diagnosis by fractionating transmission history into component parts and treat the components as separate findings. In one practice, the first step is to fractionate the transmission history into, for example, eight forms of transmission:

1. Autosomal dominant
2. Autosomal recessive
3. X-linked dominant
4. X-linked recessive
5. Mitochondrial (dominant)
6. Y-linked (dominant)
7. Contagious
8. Environmental This fractionation allows the evidence for and against each type of inheritance to be considered independently of the others. With fractionation of family history, in the example cited above, the software systems described herein determine process the following:

Patient: positive family history for autosomal recessive inheritance
Diseases: high probability for finding family history assigned in autosomal recessive diseases (since state of siblings is known)
Result: the positive family history for autosomal recessive inheritance elevates the probability of all autosomal recessive diseases, using standard Bayesian methods, just as a positive finding of "seizures" in a patient would elevate the probability of all diseases with seizures.

and

Patient: negative family history for autosomal dominant disease
Diseases: high probability for finding family history assigned for autosomal dominant inheritance (since state of parents is known)
Result: the negative family history for autosomal dominant inheritance lowers the probability of all autosomal dominant diseases, just as the absence of "seizures" in a patient would lower the probability of all diseases with seizures.

Fractionating the family history adds the high discriminative ability that is absent in simplistic models, by elevating the probability of autosomal recessive diseases and lowering the probability of autosomal dominant diseases. Given the eight types of transmission, a simple version of this fractionation model would envision eight runs of transmission information, one for each type, instead of one run with a generic transmission information. In each case the presence or absence for the particular type of transmission may be used as described above.

There is additional versatility to this process that may be understood from the example above. In many cases there is information about family history for some types of diseases and no information about family history for other types of diseases. This is illustrated by a case in which the parents are unknown but there are many affected siblings, leading to the following analysis:

Patient: positive family history for autosomal recessive inheritance
Diseases: high probability for finding family history assigned for autosomal recessive diseases
Result: the positive family history elevates the probability of all autosomal recessive diseases and Patient: "not specified" family history for autosomal dominant disease Diseases: low probability for finding family history assigned for autosomal dominant diseases (since one can't find a history if the parents are unknown)

Result: the "not specified" family history leaves unchanged the probability of all autosomal dominant diseases In the general example case the software generates eights different sets of findings of the form:

Patient: presence information for the transmission type chosen from:
  Present
  Absent
  Not specified Diseases: an array of probabilities for finding family history is assigned for diseases having the particular transmission type. The numerical values of the probabilities depend on various factors such as the number of individuals for whom state of health is known; an example of how these numbers are computed is given below.

Result: the probability of diseases with this transmission type are lowered elevated or left unchanged, depending on the correspondence between the patient information and expected diseases information, in a quantitative way depending on various factors such as the number of individuals for whom state of health is known.

Computing Probability of Finding Family History Information Using Patient Information The calculations undertaken in the processes described herein begin, in one practice, with standard probability models, but modify them to add additional information. Consider the simple case of a patient with an autosomal dominant disease having 3 older siblings and no information about the parents:

The probability of each sibling having the disease is ½ since they have a ½ chance of getting the gene from the affected parent. Therefore the probability of each sibling not having the disease is 1−½. The probability of none of the 3 siblings having the disease is $(1-½)^3$, where the caret denotes exponentiation. The probability of finding a family history in this situation is therefore $1-(1-½)^3$. In general for n siblings, the probability of finding a family history is $1-(1-½)^n$.

This standard calculation can be modified for penetrance as follows: The probability of each sibling having the disease with penetrance p is p*½ or p/2 since they have a ½ chance of getting the gene from the affected parent and a probability p of expressing the disease. Therefore the probability of each sibling not having the disease is 1−p/2. As above, this analysis leads to the general formula of $1-(1-p/2)^n$.

Similar formulas exist for other forms of transmission. Some of these probabilities depend on the gender of the patient and of the family members for whom history is known. In addition, to take into account issues such as incorrect identification of relatives, all probabilities are limited to be no less than 0.01 and no greater than 0.99.

Such calculation are modified for spontaneous mutations as follows: If the probability of the disease arising by spontaneous mutations is m, the probability of finding a family history is typically (1−m) times the probability in a similar situation in which there are no spontaneous mutations. In the autosomal dominant example above, the probability of finding a family history would be $(1-m)*(1-(1-p/2)^n)$. The analysis could be slightly more complicated in the case of autosomal recessive disease, but in practice assuming the simplification that one gene is newly mutated and the other inherited from a parent with the abnormal recessive gene serves to render the calculation similar to the calculation in autosomal dominant diseases.

These formulas could be modified further to take into account the following:

Consanguinity: If parents are from an inbred population the probability of a parent being affected by an autosomal recessive illness is higher than would otherwise be expected. Consanguinity information can include not only known cousin relations but also less direct relatedness such as family in the same village or other ethnic inbred population relationships.

Miscarriages: a high number of maternal miscarriages is found in many X-linked dominant diseases. This information could be added to information collected for each X-linked dominant disease and this information could be used to modify the expected family history in X-linked dominant diseases.

From Fractionation to Hyper-Fractionation

The above discussion of the fractionation method was simplified for the purposes of clear exposition. Instead of the 8-fold fractionation described above, with one form for each type of transmission, it is necessary to allow for at least a 16-fold hyper-fractionation, two forms for each type of transmission. The following example demonstrates the need to use hyper-fractionation with two findings for a transmission type.

Consider the analysis for an autosomal dominant disease. In the standard case (ignoring penetrance and mutations), the probability of a family history given information from one parent is ½ since the patient got the disease from a parent. Similarly, the probability of a family history given information from one sibling is ½ since the sibling has that probability of getting a gene from the affected parent, and the probability is $1-(1-½)^n$ for n siblings as derived in the previous section. How would we use information about one parent and 7 siblings in an autosomal dominant disease? Considering the parent, the probability of finding family history in that disease would be 0.5, but for the siblings the probability of finding family history would be 0.99. What probability would we use for finding a family history of this disease? The simplistic approach would be to compute the probability of finding a family history using the two partial probabilities as 1.0−(1.0−0.5)*(1.0−0.99) or 0.99. However, if all siblings were normal brothers and the father was affected, it would be improper to run the calculations as follows:

Patient: positive family history for autosomal dominant disease

Diseases: 0.99 probability for finding family history for autosomal dominant diseases Result: huge increase in the probability of all autosomal dominant diseases (due to a good fit with information that is required with 0.99 probability)

However, this is the wrong result. The many negative brothers argue strongly against the autosomal dominant diagnosis; indeed other forms of inheritance such as X-linked dominant inheritance seem much more likely since the father would transmit such diseases only to daughters. This simple fractionation model has failed because some of the autosomal dominant information needs to count as positive and some of the autosomal dominant information needs to count as negative. Accordingly, the systems and methods described herein handle this information by hyper-fractionating the calculations to do two separate calculations for autosomal dominant diseases as follows:

Patient: positive family history for autosomal dominant inheritance from the parent information Diseases: 0.5 probability for finding family history for autosomal dominant diseases, computed from the parent information Result: increase in the probability of all autosomal dominant diseases and Patient: negative family history for autosomal dominant disease from the sibling information Diseases: 0.99 probability for finding family history for autosomal dominant diseases, computed from the sibling information Result: decrease in the probability of all autosomal dominant diseases The result of these pair of analyses is to balance an increase and decrease in probability using the two different forms of evidence. In contrast, diseases with other forms of inheritance such as X-linked dominant inheritance would get an unopposed increase in probability from a similar analysis and therefore rise in relative probability over autosomal dominant diseases. This is the correct result.

Therefore, instead of using the fractionation method with as many as 8 arrays of findings about transmission, one needs to use the hyper-fractionation method to run as many as 16 chosen from a set of 32 possibilities (16 forms using either present or absent). In some implementations one could use less than the full 32 possibilities: in one implementation we use only 26 are used since the certain types of fractionation and hyper-fractionation are ignored or grouped together.

Additional hyper-hyper-fractionation beyond these 32 may need to be used, for example to implement distinguish among different relatives, possibly including others such as grandparents.

Effect of Using Transmission History in an Implementation of These Systems and Methods These approaches were used in a patient case, described in the November 2002: "Neurology Today" (publication of the American Academy of Neurology) article "How Neurologists Use the Internet to Enhance Clinical Decision-Making" by Orly Avitzur MD. "The case involved a 15-year-old boy who was first seen at age 5 with slurred speech and gait instability and who continued to deteriorate over the next 10 years with emerging marked dystonia, dysphagia, tics and seizures. On their own, the treating physician and fellow trainees came up with a long list of differential diagnoses. But after entering important variables in query form into a Web site, www.simulconsult.com, the search was narrowed considerably to Friedreich ataxia, Hallervorden-Spatz, and Huntington chorea (akinetic-rigid form). Autopsy revealed almost complete striatal atrophy with minimal cortical involvement. The final diagnosis, confirmed by CAG repeat count, was juvenile Huntington disease."

The treating doctor ran the case through the software in May 2002. By the time the article appeared in November 2002, the database for SimulConsult Neurological Syndromes had doubled in size and the correct diagnosis was listed #1 in the diagnostic probabilities ("differential diagnosis"), but other diagnoses were listed with non-trivial probability, as shown in FIG. 3. Addition of the history that the father was also affected produces the differential diagnosis in FIG. 4. Using this family history information, all diagnoses other than the correct one are reduced to insignificant, or substantially insignificant, probabilities using this transmission history. This demonstrates the practical importance of these systems and methods in a working version of software applied to a real patient case, providing information that would be useful to doctors at one of the world's top hospitals.

Display of Family History When it is Positive for Some diseases and Negative in Others The presence value (present, absent or not specified) for most finding in a patient is the same for all diseases. As shown in the FIGS. 5 and 6 describing the above case, the appearance of "seizures" at about 10 years of age is displayed as "10" for all diseases, meaning onset at 10 years.

Display of presence is not as simple for family history. A positive family history for one disease could be a negative family history for a different disease with a different inheritance pattern. For this reason, display of family history must be different than display of other findings.

As can be seen in FIG. 4, the presence of a family history is denoted in that illustration by an "F" to communicate that it is positive in some of the diseases listed and negative in others. The exact symbol used is unimportant; the point is that there needs to be some way of denoting that this history is positive in some diseases but may be negative in others.

However when a screen portrays only a single disease, the family history for that particular disease can be shown, but different values need to be displayed for different diseases, as shown in the following two examples:

Huntington chorea is an autosomal dominant disease. The family history of an affected father and no affected siblings is a positive family history for Huntington chorea for a patient and is indicated in the screen shot in FIG. 5 with a green check mark for "Family history of a similar disorder":

In contrast, Hallervorden-Spatz disease is an autosomal recessive disease, and the same family history is a negative family history for Hallervorden-Spatz disease, indicated in the screen shot in FIG. 6 with anX:

Note also that the black bar denoting the magnitude of the family history is of different length in the two screens. This is because the probability of a positive family history is different for different forms of inheritance. However, even within a particular form of inheritance there are different probabilities for different forms of evidence, as discussed in the example above that was used to introduce the need for hyper-fractionation. One could display a composite value to include both types of evidence or display the maximal of the values, as is done here. Either way, this is strictly a display choice and does not affect the computations.

The systems and methods described herein can be as software components operating on a conventional data processing system such as a Unix or Windows workstation. In that embodiment, these systems and methods may be implemented as a C language computer program, or a computer program written in any high level language including C++, Fortran, Java or Basic. The development of such programs follows from principles and skills known to those of skill in the art, and such techniques are set forth in, for example, Stephen G. Kochan, *Programming in C*, Hayden Publishing (1983).

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

The invention claimed is:

1. A method of assisting in the diagnosis of a patient in need thereof, said method comprising the steps of:

(a) providing, in a physical computing device, a set of candidate diseases and associated initial parameters representing estimated probabilities of said candidate diseases;

(b) receiving, in said computing device, a patient transmission history for said patient being diagnosed, said patient transmission history comprising information about the presence or absence of disease in one or more family members or others nearby;

(c) fractionating said patient transmission history into a plurality of forms of transmission, using said computing device, wherein said fractionating comprises determining whether there is evidence for each of said plurality of forms of transmission being present or absent in said patient transmission history, and wherein at least one of said plurality of forms of transmission is a genetic form of transmission;

(d) using said computing device to iteratively modify said initial parameters representing estimated probabilities of said candidate diseases, using the information obtained from said fractionating of said patient transmission history into each of said plurality of forms of transmission, to obtain modified parameters representing modified estimated probabilities of said candidate diseases; and (e) outputting a list capable of being displayed, said list comprising one or more of said candidate diseases having highest said modified estimated probabilities.

2. The method of claim 1, wherein step (d) comprises using a Bayesian method to obtain said modified parameters representing modified estimated probabilities of said candidate diseases.

3. The method of claim 1, wherein said genetic form of transmission is selected from the group consisting of autosomal dominant transmission, autosomal recessive transmission, X-linked dominant transmission, X-linked recessive transmission, mitochondrial dominant transmission, and Y-linked dominant transmission.

4. The method of claim 1, wherein at least a second of said plurality of forms of transmission is selected from the group consisting of contagious transmission and environmental transmission.

5. The method of claim 1, wherein said plurality of forms of transmission are selected from the group consisting of autosomal dominant transmission, autosomal recessive transmission, X-linked dominant transmission, X-linked recessive transmission, mitochondrial dominant transmission, Y-linked dominant transmission, contagious transmission, and environmental transmission.

6. The method of claim 1, wherein said method results in the diagnosis of said patient as having one of said candidate diseases having highest said modified estimated probabilities.

7. The method of claim 1, wherein step (d) comprises modifying each of said initial parameters representing estimated probabilities of said candidate diseases, using the information obtained from said fractionating of said patient transmission history into each of said plurality of forms of transmission, to obtain modified parameters representing modified estimated probabilities of said candidate diseases.

8. The method of claim 1, wherein step (e) comprises transmitting said list over the Internet.

9. The method of claim 1, wherein step (e) comprises outputting said list to a display device.

10. The method of claim 9, further comprising outputting to said display device said modified estimated probabilities of said one or more candidate diseases having highest said modified estimated probabilities in rank order.

11. The method of claim 1, wherein said plurality of forms of transmission comprise at least eight forms of transmission.

12. The method of claim 1, wherein step (c) comprises evaluating at least 16 types of said evidence for said plurality of forms of transmission.

13. The method of claim 1, wherein step (c) comprises evaluating at least 26 types of positive or negative evidence for or against said plurality of forms of transmission.

14. The method of claim 1, wherein step (c) comprises determining whether there is evidence for each of said plurality of forms of transmission being present or absent in said patient transmission history, based on the sibling information obtained from said patient transmission history.

15. The method of claim 1, wherein step (c) comprises determining whether there is evidence for each of said plurality of forms of transmission being present or absent in said patient transmission history, based on the parent information obtained from said patient transmission history.

16. The method of claim 1, wherein step (a) further comprises providing factors accounting for mutation, penetrance, or error probabilities for each said candidate disease, and step (d) comprises using said factors to iteratively modify said initial parameters representing estimated probabilities of said candidate diseases, using the information obtained from said fractionating of said patient transmission history into each of said plurality of forms of transmission, to obtain modified parameters representing modified estimated probabilities of said candidate diseases.

17. The method of claim 1, wherein said patient transmission history comprises information about parental consanguinity or miscarriages.

18. The method of claim 1, wherein said patient transmission history comprises information about maternal uncles, more distant relatives, non-related contacts, or persons sharing exposure to the same environment.

19. The method of claim 1, wherein said patient transmission history consists of information about the presence or absence of disease in one or more family members or others nearby.

20. The method of claim 1, wherein said associated initial parameters are estimated probabilities of said candidate diseases.

21. The method of claim 20, wherein said modified parameters are modified estimated probabilities of said candidate diseases.

22. The method of claim 1, wherein said physical computing device is Unix-based or Windows-based.

23. The method of claim 1, wherein said physical computing device is accessed and operated over the Internet.

24. The method of claim 1, wherein step (d) comprises computing a probability of expecting a patient transmission history for a particular form of transmission in the patient being diagnosed depending on evidence for presence or absence for each said form of transmission in said patient transmission history and using each said form of transmission to modify said initial parameters representing estimated probabilities of said candidate diseases to obtain said modified parameters representing modified estimated probabilities of said candidate diseases.

25. The method of claim 24, wherein said genetic form of transmission is selected from the group consisting of autosomal dominant transmission, autosomal recessive transmission, X-linked dominant transmission, X-linked recessive transmission, mitochondrial dominant transmission, and Y-linked dominant transmission.

26. The method of claim 24, wherein step (e) comprises outputting said list to a display device.

27. The method of claim 26, further comprising outputting to said display device said modified estimated probabilities of said one or more candidate diseases having highest said modified estimated probabilities in rank order.

28. The method of claim 24, wherein step (c) comprises determining whether there is evidence for each of said plurality of forms of transmission being present or absent in said patient transmission history, based on the sibling information obtained from said patient transmission history.

29. The method of claim 24, wherein step (c) comprises determining whether there is evidence for each of said plurality of forms of transmission being present or absent in said patient transmission history, based on the parent information obtained from said patient transmission history.

30. The method of claim 24, wherein step (a) further comprises providing factors accounting for mutation, penetrance, or error probabilities for each said candidate disease, and step (d) comprises using said factors to iteratively modify said initial parameters representing estimated probabilities of said candidate diseases, using the information obtained from said fractionating of said patient transmission history into each of said plurality of forms of transmission, to obtain modified parameters representing modified estimated probabilities of said candidate diseases.

31. The method of claim 24, wherein said patient transmission history comprises information about parental consanguinity or miscarriages.

32. The method of claim 24, wherein said patient transmission history comprises information about maternal uncles, more distant relatives, non-related contacts, or persons sharing exposure to the same environment.

33. The method of claim 24, wherein said associated initial parameters are estimated probabilities of said candidate diseases.

34. The method of claim 33, wherein said modified parameters are modified estimated probabilities of said candidate diseases.

35. A computer readable medium having stored thereon instructions for directing a physical computing device to implement a method of assisting in the diagnosis of a patient in need thereof, the instructions comprising the steps of:
  (a) providing, in said computing device, a set of candidate diseases and associated initial parameters representing estimated probabilities of said candidate diseases;
  (b) receiving, in said computing device, a patient transmission history for said patient being diagnosed, said patient transmission history comprising information about the presence or absence of disease in one or more family members or others nearby;
  (c) fractionating said patient transmission history into a plurality of forms of transmission, using said computing device, wherein said fractionating comprises determining whether there is evidence for each of said plurality of forms of transmission being present or absent in said patient transmission history, and wherein at least one of said plurality of forms of transmission is a genetic form of transmission;
  (d) using said computing device to iteratively modify said initial parameters representing estimated probabilities of said candidate diseases, using the information obtained from said fractionating of said patient transmission history into each of said plurality of forms of transmission, to obtain modified parameters representing modified estimated probabilities of said candidate diseases; and
  (e) outputting a list capable of being displayed, said list comprising one or more of said candidate diseases having highest said modified estimated probabilities.

36. The computer readable medium of claim 35, wherein step (d) comprises computing a probability of expecting a patient transmission history for a particular form of transmission in the patient being diagnosed depending on evidence for presence or absence for each said form of transmission in said patient transmission history and using each said form of transmission to modify said initial parameters representing estimated probabilities of said candidate diseases to obtain said modified parameters representing modified estimated probabilities of said candidate diseases.

37. A physical computing device for assisting in the diagnosis of a patient in need thereof, said computing device comprising:
  (a) a set of candidate diseases and associated initial parameters representing estimated probabilities of said candidate diseases;
  (b) means for receiving a patient transmission history for said patient being diagnosed, said patient transmission history comprising information about the presence or absence of disease in one or more family members or others nearby;
  (c) means for fractionating said patient transmission history into a plurality of forms of transmission, wherein said fractionating comprises determining whether there is evidence for each of said plurality of forms of transmission being present or absent in said patient transmission history, and wherein at least one of said plurality of forms of transmission is a genetic form of transmission;
  (d) means for iteratively modifying said initial parameters representing estimated probabilities of said candidate diseases, using the information obtained from said fractionating of said patient transmission history into each of said plurality of forms of transmission, to obtain modified parameters representing modified estimated probabilities of said candidate diseases; and
  (e) means for outputting a list capable of being displayed, said list comprising one or more of said candidate diseases having highest said modified estimated probabilities.

* * * * *